United States Patent [19]

Kleiner et al.

[11] 4,401,473

[45] Aug. 30, 1983

[54] USE OF DIMETHYLPHOSPHINYLALKANEPHOSPHONIC ACID AS A SETTING RETARDER IN GYPSUM

[75] Inventors: Hans-Jerg Kleiner, Kronberg; Volker Knittel, Wiesbaden; Gerhard Debus, Ruedesheim, all of Fed. Rep. of Germany

[73] Assignee: Hoechst Aktiengesellschaft, Fed. Rep. of Germany

[21] Appl. No.: 351,576

[22] Filed: Feb. 23, 1982

Related U.S. Application Data

[62] Division of Ser. No. 283,511, Jul. 15, 1981.

[30] Foreign Application Priority Data

Jul. 17, 1980 [DE] Fed. Rep. of Germany ....... 3027040

[51] Int. Cl.³ .................... C04B 11/00; C04B 11/14; C01F 11/46
[52] U.S. Cl. .................... 106/109; 106/111; 106/315; 423/265; 423/555
[58] Field of Search ............ 423/555, 265; 106/109, 106/110, 111, 315

[56] References Cited

U.S. PATENT DOCUMENTS

| | | | |
|---|---|---|---|
| 3,646,133 | 2/1972 | Kerst | 260/545 P |
| 3,925,456 | 12/1975 | Ploger et al. | 106/109 |
| 3,941,772 | 3/1976 | Ploger et al. | 106/111 |
| 3,960,888 | 6/1976 | Ploger et al. | 423/555 |
| 4,225,361 | 9/1980 | Joseph | 106/111 |
| 4,260,422 | 4/1981 | Thamm et al. | 106/111 |

OTHER PUBLICATIONS

Maier, L., Preparation & Properties of Bis(Phosphonylmethyl)Phosphinates and Bis(Dihydroxylphosphonylmethyl)Phosphinic Acid, Angew. Chem. International Edit., vol. 7, 1968, #5, pp. 384–385.

Maier, L., Preparation and Properties of Tris(Phosphonylmethyl) Phosphine Oxides and the Corresponding Acids, Angew. Chem. Internat. Edit., vol. 7, 1968, #5, pp. 385–386.

Kabachnik et al., Synthesis and Properties of Some Ethylene Diphosphoryl Compounds Investiya Akademil Nauk USSR, #10, pp. 2290–2295, Oct. 1974 (Translation).

*Primary Examiner*—Gary P. Straub
*Attorney, Agent, or Firm*—James E. Bryan

[57] ABSTRACT

The invention relates to dimethylphosphinylalkanephosphonic acids of the general formula I, in which n is 1 or 2, which are used as setting retarders for gypsum.

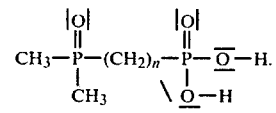

1 Claim, No Drawings

USE OF DIMETHYLPHOSPHINYLALKANEPHOSPHONIC ACID AS A SETTING RETARDER IN GYPSUM

This is a division of application Ser. No. 283,511, filed July 15, 1981.

This invention relates to dimethylphosphinylalkanephosphonic acids, a process for the preparation of these compounds and the use thereof as setting retarders in gypsum or in mixtures containing gypsum.

For a fairly long time substituted or unsubstituted alkanephosphonic acids and dialkylphosphinic acids have been of importance as precursors, intermediate products and end products in numerous specialized fields, for example as complex-forming agents, plant protection agents, textile auxiliaries, antistatic agents, flameproofing agents, anticorrosion agents, plasticizers for plastics or flotation auxiliaries; their use as setting retarders for gypsum also has already been suggested.

An example of a flame-retarding component in polyamide molding compositions is (dimethylphosphinylmethyl)-methylphosphinic acid

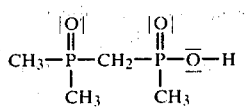

(see German Offenlegungsschrift No. 2,523,145, which is equivalent to U.S. Pat. No. 4,062,828), which is described in detail below. The setting retarders for gypsum which are already known also include 3,3-diphosphonopimelic acid

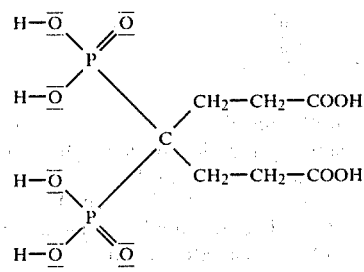

which is described in German Offenlegungsschrift No. 2,647,042, referred to below.

The fields of application relevant to the present invention include, in particular, the end use as setting retarders for gypsum. Gypsums are defined as inorganic, mineral materials which are composed of at least 50 percent by weight of dehydration products of calcium sulfate dihydrate and into which a very wide variety of additives can be mixed (in this context see, for example, "Baugipse" ("Building Plasters"), DIN Standard 1168, Sheet 1 dated May 1975 and Part 2 dated July 1975, or F. Graf and F. Rausch, "Gipshilfsprodukte, ihre Anwendung und Wirkung" ("Auxiliary Products for Gypsum, Their Use and Their Action") in Zement-Kalk-Gips, Bau Verlag—Wiesbaden, Issue 5, No. 5-1951, pages 1 to 7). When stirred with water, gypsums produce a composition which solidifies gradually (=setting) and which has a firm consistency; in practice, the setting rate of the gypsum compositions is of central importance in this respect, since this, of course, affects the processing properties and the processing time.

The compounds known from the state of the art which retard the setting rate (time) of gypsum which has been stirred with water also include, as well as organic polymers such as casein and gelatin, organic carboxylic acids, such as citric acid, malic acid and tartaric acid, or inorganic acids, such as boric acid and phosphoric acid; the use of these in the form of their salts is also known. Organic phosphorus compounds have also already been described in the relevant literature as setting retarders for gypsum.

The publications which follow, which describe processes for the preparation of such compounds, the compounds themselves and/or their fields of application, are examples of relevant publications which are known from the state of the art:

German Pat. No. 2,441,783 (equivalent to U.S. Pat. No. 4,069,247) describes a process for the preparation of phosphonic and/or phosphinic acids by hydrolytic cleavage of phosphonic and/or phosphinic acid alkyl esters (the alkyl radical having 2 or more carbon atoms) at temperatures from 170° to 300° C., using at least the quantity of water which is required by stoichiometry for the hydrolysis, the alkanol formed as one of the hydrolysis products being removed from the reaction mixture by distillation. The reaction is carried out in such a way that it starts in the presence of at least 2 percent by weight of the acid; educts which are typical of this process are n-butanephosphonic acid di-n-butyl ester or methylethylphosphinic acid ethyl ester, from which the corresponding acids are then formed:

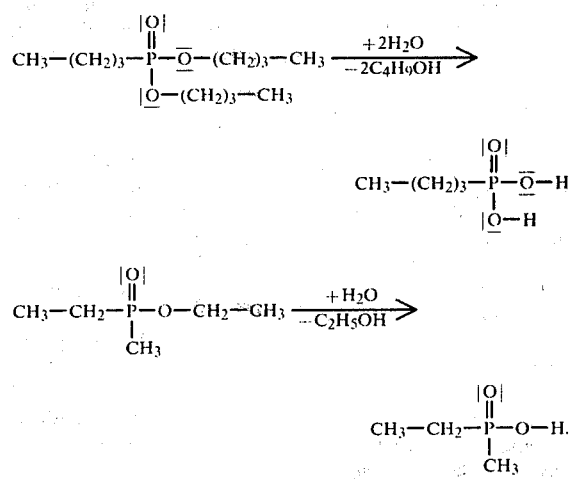

The process claimed in German Pat. No. 2,441,878 (equivalent to U.S. Pat. No. 4,069,245) differs from the process described earlier in that the starting material employed is a phosphonic and/or phosphinic acid methyl ester and the temperature during the reaction is 160° to 250° C.

German Offenlegungsschrift No. 2,719,385, discloses a process for the preparation of phosphonic and phosphinic acids by acidolytic cleavage of the alkyl esters thereof, using an alkylcarboxylic, alkenylcarboxylic, cycloalkylcarboxylic or phenylcarboxylic acid or formic acid in a quantity at least equivalent to the alkyl ester groups, if appropriate in the presence of catalytic amounts of strong acids or bases. The reaction is carried out at 100° to 200° C. and the carboxylic acid alkyl ester formed as one of the products of the acidolytic cleavage is removed from the reaction mixture by distillation; educts which are typical of this process are carboethoxymethane-phosphonic acid diethyl ester or methanediphosphonic acid tetraethyl ester, and the corresponding acids are then formed from these using, for example, acetic acid:

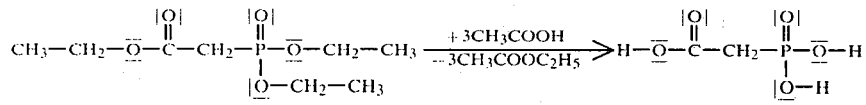

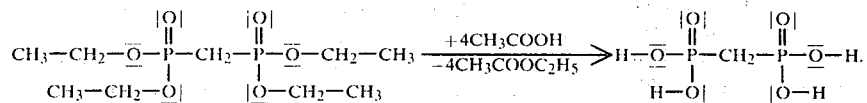

U.S. Pat. No. 3,646,133, describes anhydrides of organic alkylidenephosphonylphosphine oxides (or phosphinylalkanephosphonic acids), the free acids of which can be described, inter alia, by means of the general formula

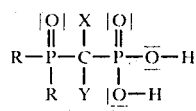

wherein R is, inter alia, a $C_1$ to $C_{18}$ alkyl radical; X and Y are hydrogen or $C_1$ to $C_6$ alkyl groups. The compounds named in concrete terms also include (Example 10) diethylphosphinylmethanephosphonic acid as a compound having the lowest number of carbon atoms in the radical R. However, the reference in column 4, lines 49/50 of U.S. Pat. No. 3,646,133, to three brief communications by L. Maier in Angew. Chem., 80, 1968, No. 10, pages 400–402 (equivalent to Angew. Chem. International Edition 7, No. 5, pages 384–386) on organic alkylidenephosphonylphosphine oxides does not provide any information on monophosphonylphosphine oxides (equivalent to phosphinylphosphonic acids), but only on di and tri derivatives.

The publication by M. I. Kabachnik, T. Y. Medved', I. B. Goryunova, L. I. Tikhonova and E. I. Matrosov in Izv. Akad. Nauk. USSR, Ser. Khim. 1974, 10, pages 2290 to 2295, discloses the reaction of diethylphosphine oxide with vinylphosphonic acid diethyl ester, and according to this publication the reaction can be followed by an acid hydrolysis of the phosphinylethanephosphonic acid ester formed in the reaction to give 2-diethylphosphinylethanephosphonic acid.

German Offenlegungsschrift No. 2,523,145 (equivalent to U.S. Pat. No. 4,062,828) describes a polyamide molding composition of low inflammability containing, as the flame-retarding component, phosphinylphosphine acids which are represented by the following general formula

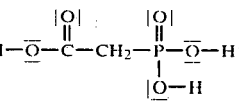

in which $R^1$ denotes $C_1$ to $C_{16}$ alkyl radicals, $C_6$ to $C_{16}$ aryl radicals or aralkyl radicals, $R^2$ denotes $C_1$ to $C_8$ alkylene groups, or arylene groups, and n denotes an integer from 1 to 3; typical representatives of the class of compounds described are (dimethylphosphinylmethyl)-methylphosphinic acid (n=1, $R^1$=$CH_3$ and $R^2$=$CH_2$) or (methylphosphinyldimethylene)-dimethyldiphosphinic acid (n=2, $R^1$=$CH_3$ and $R^2$=$CH_2$).

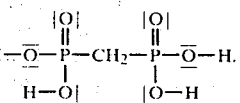

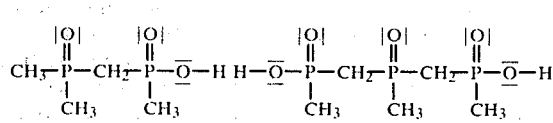

The phosphonic-carboxylic acid compounds according to German Offenlegungsschrift No. 2,647,042, which are represented by the following general formula (R = $C_1$ to $C_{18}$ alkyl, substituted by halogen if appropriate; H, an alkali metal ion or an ammonium ion)

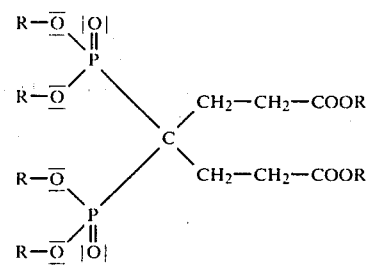

can be prepared from the methylenediphosphonic acid tetra-alkyl esters by reaction with acrylic acid esters in a molar ratio of about 1 to 2 in the presence of strongly basic catalysts at 0° to 140° C., followed by transesterification or hydrolysis under acid or alkaline conditions. One of the fields of application for phosphonic-carboxylic acid compounds in which R denotes only H or an alkali metal and/or ammonium ion, is their use as setting retarders for gypsum.

European Published Specification No. 0,000,061 discloses phosphonic-carboxylic acid compounds which are described, inter alia, by the following general formula ($R^1$ = H, alkyl or an alkali metal ion or an ammonium ion; $R^2$ = alkyl)

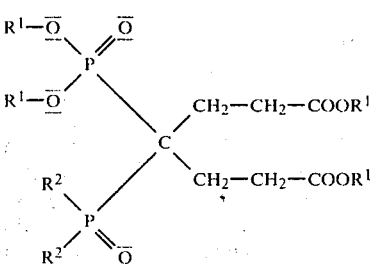

They can be prepared from the dialkylphosphinylmethanephosphonic acid diesters by reaction with acrylic acid esters in the presence of strongly basic catalysts at 0° to 140° C., followed, if appropriate, by transesterification or hydrolysis under acid or alkaline conditions. One of the fields of application for phosphonic-carboxylic acid compounds in which $R^1$ denotes only H or an alkali metal and/or ammonium ion, is their use as setting retarders for gypsum. The dialkylphosphinylalkanephosphonic acids which have been described in concrete terms in the state of the art include only compounds in which the alkyl substituents on the phosphinyl radical have at least 2 carbon atoms, that is to say they constitute at least an ethyl group, and compounds having two methyl groups have hitherto not been disclosed. In addition, although the known phosphonic-carboxylic acid compounds exhibit a certain retardation of the setting rate of gypsum, they have to be prepared in a relatively tedious manner from the phosphinylmethanephosphonic acid ester parent substances.

The object of the present invention is, therefore, to provide dimethylphosphinylalkanephosphonic acids for the first time. Compared with the compounds which are known from the state of the art, these compounds are intended, in particular, to produce a significant retardation of the setting of gypsum and, compared with compounds of similar structure and similar action, to be relatively easier to prepare.

This problem is solved in accordance with the invention by providing dimethylphosphinylalkanephosphonic acids of the general formula I

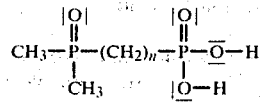

in which n is 1 or 2; in particular, n is 1. The compounds of the general formula I include dimethylphosphinylmethanephosphonic acid and dimethylphosphinylethanephosphonic acid.

The compounds according to the invention can be prepared by acidolysis or hydrolysis from dimethylphosphinylalkanephosphonic acid esters of the general formula II

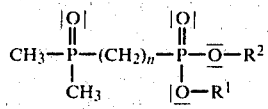

in which n is 1 or 2 and $R^1$ and $R^2$ are identical or different and denote $C_1$ to $C_8$ alkyl groups, preferably $C_1$ to $C_3$ alkyl groups. Some of these esters are disclosed in the publications mentioned as belonging to the state of the art, or can be prepared by analogy with the processes mentioned in these publications. The acidolysis of the diesters can be effected, for example, by means of hydrogen chloride, if appropriate in the presence of water, or by reaction with organic carboxylic acids in the presence of catalysts, according to the teaching of German Offenlegungsschrift No. 2,719,385, which already has been mentioned. The hydrolysis is appropriately carried out by the processes of German Pat. No. 2,441,783 (equivalent to U.S. Pat. No. 4,069,247) and No. 2,441,878 (equivalent to U.S. Pat. No. 4,069,245), which have also already been mentioned, by reaction with water above a temperature of about 160° to 170° C.

The following are examples of compounds of the general formula II: dimethylphosphinylmethanephosphonic acid dimethyl, diethyl and diisopropyl esters and 2-dimethylphosphinylethanephosphonic acid dimethyl, diethyl and di-n-propyl esters.

The dimethylphosphinylalkanephosphonic acids according to the invention are preferably used as setting retarders for gypsum, in particular in an amount of 0.005 to 0.5 percent by weight, preferably 0.01 to 0.1 percent by weight, in each case relative to the content of gypsum in mixtures containing gypsum or relative to pure gypsum. The term "mixtures containing gypsum" is to be understood in this context as meaning, in particular, varieties of building plaster, such as molding plaster, gypsum plaster, ready-mixed gypsum plaster, bond gypsum plaster, machine gypsum plaster, ramming plaster, pointing plaster or grouting plaster, which, in addition to at least 50 percent by weight of dehydrated calcium sulfate dihydrate, can also contain other components, such as hydrated lime, extenders (that is to say substances which affect the property of the plaster, for example its consistency, its adhesion or its stiffening) and fillers, such as sand or perlites. Compared with the organic carboxylic acids which are known in the industry and hitherto have been preferentially employed, the compounds according to the invention exhibit a significantly higher retardation of setting, and this is also true—if comparable quantities are used—compared with known organophosphorus compounds. In addition, they can be synthesized more easily than the compounds which are known for this field of application.

The invention will be further illustrated by reference to the following specific examples:

EXAMPLE 1

1.1 Preparation of dimethylphosphinylmethanephosphonic acid diethyl ester 252 g of chloromethyl-dimethylphosphine oxide are heated to 140° to 150° C. under an atmosphere of nitrogen and 480 g of triethylphosphite are added dropwise in the course of 4 hours. Stirring is continued for a further 1.5 hours at the temperature indicated, 98 g of ethyl chloride (76% of theoretical) being collected in a cold trap connected downstream of the apparatus. The mixture is then incipiently distilled at 0.6 mm Hg until the internal temperature reaches 148° C., with distillate passing over at a temperature of 135° C. This gives 309 g of the ester, having a solidification point of 59°–60° C. (yield: 68 percent of theoretical). The product can be employed for further reactions in the form of the crude product; further purification can be effected by distillation (boiling point at 0.4 mm Hg: 140° C.).

1.2 Preparation of dimethylphosphinylmethanephosphonic acid 1.2.1 by acidolysis using hydrochloric acid 618 g of concentrated hydrochloric acid are added to 309 g of dimethylphosphinylmethanephosphonic acid diethyl ester and the mixture is kept at 100° C. for approximately 15 hours, hydrogen chloride gas being passed in at the same time. Material is then distilled off, first under a water pump vacuum at 100° C. and finally under 1 mm Hg until an internal temperature of 160° C. is reached. There is a residue of 226 g (yield: 100% of theoretical); after recrystallization from acetic acid the product has a melting point of 160° C. to 161° C.

Analysis: $C_3H_{10}O_4P_2$; (172); calculated: C: 20.95%; H: 5.82%; P: 36.1%; found: C: 21.0%; H: 5.8%; P: 35.5%.

1.2.2 by acidolysis using acetic acid 50 g of glacial acetic acid and 5.6 g of concentrated sulfuric acid are added to 280 g of dimethylphosphinylmethanephosphonic acid diethyl ester and the mixture is heated at 145° to 155° C. A further 230 g of glacial acetic acid are added dropwise in the course of 10 hours, while ethyl acetate is distilled off through a distillation column. The mixture is then cooled, the crystals which have been precipitated are filtered off, the filtrate is concentrated and further product is filtered off; 140 g of the acid are obtained (yield: 66.5% of theoretical).

1.2.3 by hydrolysis using water:

3 g of dimethylphosphinylmethanephosphonic acid are added to 250 g of dimethylphosphinylmethanephosphonic acid diethyl ester and the mixture is heated at 170° C. Water is now added dropwise, while ethanol is distilled off through a column. After 6 hours approximately 95 g of ethanol, mixed with a little diethyl ether, have been removed by distillation. This gives 205 g of product, having a water content of 6.35% (yield: 100% of theoretical). After recrystallization from acetic acid, the product has a melting point of 157° to 160° C.

EXAMPLE 2

2.1 Preparation of 2-dimethylphosphinylethanephosphonic acid dimethyl ester 95 g of vinyldimethylphosphine oxide are dissolved in dioxane and rendered alkaline with sodium methoxide solution. 100 g of dimethyl phosphite are added dropwise, in an exothermic reaction. The mixture is then subjected to fractional distillation, which gives 104 g of product, boiling point at 0.4 mm Hg: 182° C. (yield: 53% of theoretical). The first runnings of the distillation contain unreacted dimethyl phosphite and vinyldimethylphosphine oxide, which can be used again in a further batch.

2.2 Preparation of 2-dimethylphosphinylethanephosphonic acid by acidolysis using hydrochloric acid Concentrated hydrochloric acid is added to 104 g of 2-dimethylphosphinylethanephosphonic acid dimethyl ester and the mixture is kept at 100° C., hydrogen chloride gas being passed through at the same time. When the reaction is complete, material is distilled off under a water pump vacuum until an internal temperature of 130° C. is reached. The crystalline residue is recrystallized from ethanol containing a very small quantity of water, giving 70 g of a product having a melting point of 164° to 166° C. (yield: 77.5% of theoretical).

Analysis: $C_4H_{12}O_4P_2$; (186); calculated: C: 25.18%; H: 6.45%; P: 33.33%; found: C: 25.8%; H: 6.6%; P: 33.4%.

EXAMPLES 3 AND 4 AND COMPARISON EXAMPLES V1 TO V4

The figures shown in the table which follows of the effect on the setting time of the samples investigated were determined by the "Vicat" method as specified in DIN 1168, Part 2, in the text of July 1975 ("Testing by Means of the Plunger Cone" under item 2.5.2). In this process for determining the commencement of stiffening of mixtures containing gypsum, a measure of the commencement of stiffening is obtained by determining the time in minutes after which a plunger cone remains at a specific height when it penetrates into a sample of plaster. The time is calculated from the commencement of feeding in the mixture. This is effected by mixing the samples containing the plaster and the setting retarder with water, until free from lumps, in a sample: water ratio of 10:6. The end of the stiffening (the setting time) is taken as the point in the measurement at which the plunger cone penetrates no further into the sample of plaster. The same employed is either molding plaster (a dehydration product of calcium sulfate dihydrate in the low temperature range) (type 1) or a mixture of 95% by weight of molding plaster and 5% by weight of hydrated lime (type 2).

Regarding the compounds employed in Comparison Examples V1 and V2, citric acid and tartaric acid, respectively, it is known that, if citric acid is used in plaster compositions containing lime (for example type 2) or if tartaric acid is used in plaster compositions not containing lime (for example type 1), they will in each case give values of setting time which are up to about 50% lower than is the case in the respective opposite type. They were, therefore, employed in the composition which was more advantageous for them and comparison was made with these relatively better values. In contrast with these organic carboxylic acids, both of the dialkylphosphinylalkanephosphonic acids according to the invention can be employed with good results in both types of plaster composition. The comparison tests against the known organophosphorus compounds of comparable structure V3 and V4) also show that at least the dimethylphosphinylmethanephosphonic acid employed in Example 3 produces a retarding action which is at least comparable, when using only half the quantity of retarder added.

| Example or comparison example of setting retarder | Quantity of setting retarder in % by weight (relative to the quantity of plaster) | Setting time in plaster of type 1 (minutes) | | Setting time in plaster of type 2 (minutes) | |
|---|---|---|---|---|---|
| | | Start | End | Start | End |
| Dimethylphosphinylmethanephosphonic acid (Example 1) | 0.050 | still not set after 1,320 minutes | | Still not set after 480 minutes | |
| | 0.025 | 315 | 330 | 154 | 168 |
| | 0.020 | 270 | 281 | 138 | 150 |
| 2-Dimethylphosphinylethanephosphonic acid (Example 2) | 0.050 | 160 | 174 | 56 | 70 |
| Citric acid(*) | 0.100 | 205 | 225 | — | — |
| (V1) | 0.050 | 105 | 116 | — | — |

| Example or comparison example of setting retarder | Quantity of setting retarder in % by weight (relative to the quantity of plaster) | Setting time in plaster of type 1 (minutes) | | Setting time in plaster of type 2 (minutes) | |
|---|---|---|---|---|---|
| | | Start | End | Start | End |
| Tartaric acid[*] (V2) | 0.050 | — | — | 173 | 253 |
| 3-Dimethylphosphinyl-3-phosphonopimelic acid[**] | 0.100 | still not set after 1,800 minutes | | — | — |
| (V3) | 0.050 | 330 | 360 | — | — |
| 3,3-Diphosphonopimelic acid[***] | 0.100 | still not set after 390 minutes | | — | — |
| (V4) | 0.075 | 185 | 200 | — | — |

[*] Published in the article by F. Graf and F. Rausch, Zement-Kalk-Gips (see introduction); the values were co-determined in a series of tests
[**] European Published Specification 0,000,061, values taken from the table on page 27
[***] German Offenlegungsschrift No. 2,647,042, values taken from the table on page 12.

It will be obvious to those skilled in the art that many modifications may be made within the scope of the present invention without departing from the spirit thereof, and the invention includes all such modifications.

What is claimed is:

1. Gypsum containing, as a setting retarder, a dimethylphosphinylalkanephosphonic acid of the general formula I

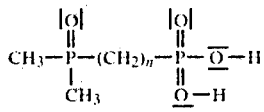

in which n is 1 or 2.